(12) United States Patent
Davis et al.

(10) Patent No.: US 11,097,081 B2
(45) Date of Patent: Aug. 24, 2021

(54) DUAL DUROMETER SOFT/FLEXIBLE ENHANCED BOND STRENGTH GUIDING TIP

(75) Inventors: Scott A. Davis, Southboro, MA (US); Eric Schneider, Lincoln, RI (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2190 days.

(21) Appl. No.: 13/536,477

(22) Filed: Jun. 28, 2012

(65) Prior Publication Data
US 2013/0012924 A1    Jan. 10, 2013

Related U.S. Application Data

(60) Provisional application No. 61/504,966, filed on Jul. 6, 2011.

(51) Int. Cl.
| | |
|---|---|
| A61M 25/00 | (2006.01) |
| B29C 45/16 | (2006.01) |
| A61L 29/06 | (2006.01) |
| B29C 45/14 | (2006.01) |
| B29C 45/00 | (2006.01) |
| B29L 31/00 | (2006.01) |

(52) U.S. Cl.
CPC .......... *A61M 25/001* (2013.01); *A61L 29/06* (2013.01); *A61M 25/008* (2013.01); *B29C 45/1671* (2013.01); *B29C 45/1676* (2013.01); *B29C 45/0062* (2013.01); *B29C 45/14065* (2013.01); *B29C 45/14614* (2013.01); *B29L 2031/7542* (2013.01)

(58) Field of Classification Search
CPC ... A61M 25/001; A61M 25/008; A61L 29/06; B29C 45/1671; B29C 45/0062; B29C 45/14065; B29L 2031/7542
See application file for complete search history.

(56) References Cited

U.S. PATENT DOCUMENTS

| | | | |
|---|---|---|---|
| 6,743,219 B1 | 6/2004 | Dwyer et al. | |
| 7,029,467 B2 | 4/2006 | Currier et al. | |
| 7,575,568 B2 | 8/2009 | Holman et al. | |
| 2004/0015138 A1* | 1/2004 | Currier | ............ A61M 25/0068 604/264 |
| 2007/0219466 A1 | 9/2007 | Tremulis et al. | |
| 2008/0108975 A1* | 5/2008 | Appling | ............. A61M 25/003 604/532 |
| 2008/0275426 A1 | 11/2008 | Holman et al. | |

OTHER PUBLICATIONS

Versatile Processing, pebax Polyether Block Amides, http://web.archive.org/web/20070622121619/http://www.pebax.com/sites/pebax/en/properties/versatile_processing.page, retrieved by archive.org on Jun. 22, 2007; viewed Sep. 26, 2012.

\* cited by examiner

*Primary Examiner* — Lauren P Farrar
(74) *Attorney, Agent, or Firm* — Seager, Tufte & Wickhem, LLP

(57) ABSTRACT

A catheter having a distal tip comprising two sections of different hardness, and a method of making the same, is herein disclosed. The first section of the two sections is distal to the second section of the two sections and the second section is comprised of a material that is harder than the material of the first section. Additionally, the distal tip is bonded to a catheter shaft and the material of the catheter shaft is harder than the material of the first and second sections. The material of the catheter shaft, first section, and second section can comprise polyether block amide, with each section and the catheter shaft having different properties.

20 Claims, 3 Drawing Sheets

DUAL DUROMETER SOFT/FLEXIBLE ENHANCED BOND STRENGTH GUIDING TIP

CROSS-REFERENCE TO RELATED APPLICATIONS

Figure 1:
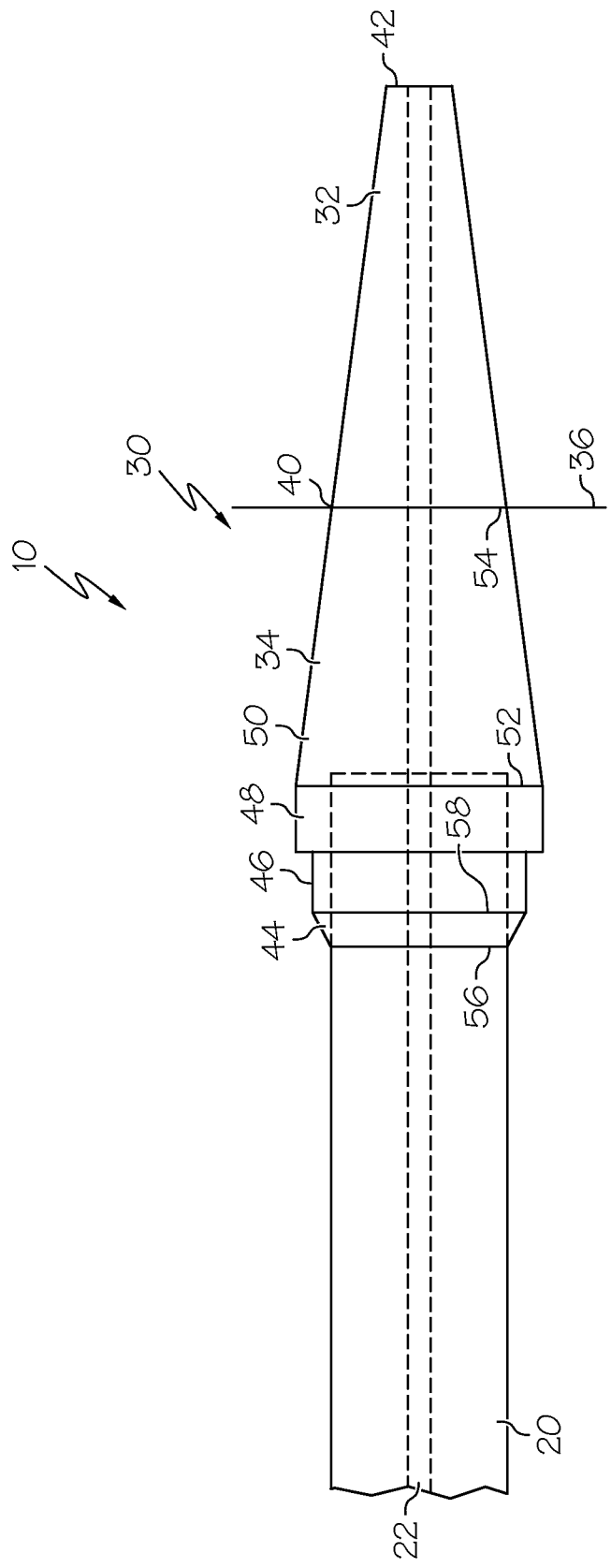

This Application claims priority to U.S. Provisional Application No. 61/504,966, filed Jul. 6, 2011, the entire contents of which are herein incorporated by reference.

STATEMENT REGARDING FEDERALLY SPONSORED RESEARCH

Not Applicable.

FIELD OF THE INVENTION

This invention relates to a catheter shaft and tip and method of making the same, and more particularly to a catheter tip having discrete portions of different hardness.

BACKGROUND OF THE INVENTION

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

Various forms of catheter shafts and tips are known in the art. Moreover, it is known to construct catheter shafts and tips out of flexible polymeric materials. Previously known catheter shafts and tips can suffer from separation at the shaft-tip interface, particularly where the material used for the shaft is significantly different from that of the tip. Alternatively, catheters utilizing the same material for the shaft and tip can suffer from various performance deficiencies. For example, in instances where the tip and shaft are formed of the same material, the tip may be undesirably stiff or hard, which can cause damage to the patient's vasculature, esophagus, bilary, colonic, duodenal strictures, or other internal organs. Conversely, the shaft and tip can be formed out of a softer material, common to both the shaft and tip, which is potentially less harmful to the patient's organs but has reduced pushability.

In light of the foregoing, there remains a need for a catheter shaft and tip that have good adherence to one another, while simultaneously providing an atraumatic tip and shaft with requisite strength and pushability.

BRIEF SUMMARY OF THE INVENTION

In at least one embodiment, a catheter comprises a catheter shaft and a catheter tip. The catheter shaft comprises a polyether block amide material and the catheter tip also comprises a polyether block amide material. The catheter tip further comprises a first longitudinal section and a second longitudinal section, and the first longitudinal section is formed of polyether block amide having a first durometer. The second longitudinal section is formed of a polyether block amide having a second durometer greater than the first durometer. The first longitudinal section is distal to the second longitudinal section and the second longitudinal section is bonded to the catheter shaft and to the first longitudinal section. In addition, the polyether block amide material of the catheter shaft has at least a third durometer greater than the second durometer. At least a portion of the first longitudinal section is tapered and at least a portion of the second longitudinal section is tapered.

In some embodiments, the material of the first longitudinal section has a durometer between 20 and 30 shore D.

In some embodiments, the material of the second longitudinal section has a durometer between 30 and 42 shore D.

In some embodiments, the material of the catheter shaft has a durometer between 55 and 70 shore D. In some embodiments, the material of the first longitudinal section has a durometer of 27 shore D and the material of the catheter shaft has a durometer of 64 shore D.

In some embodiments, the second longitudinal section comprises a proximal portion, a first cylindrical portion, a second cylindrical portion, and a frusto-conical portion. The first cylindrical portion is distal to the proximal portion, the second cylindrical portion is distal to the first cylindrical portion, and the frusto-conical portion is distal to the second cylindrical portion and proximal to the first longitudinal section.

In some embodiments, the proximal portion has a circular cross-section and its diameter increases from its proximal end to its distal end.

In some embodiments, the distal end of the catheter shaft extends distally beyond the proximal portion, first cylindrical portion, and second cylindrical portion and into the frusto-conical portion.

In some embodiments, the catheter tip has a length and each of the first longitudinal section and second longitudinal section is one-half the length.

In some embodiments, the frusto-conical portion and the first longitudinal section have the same rate of taper.

In some embodiments, a method of forming a catheter comprises extruding a catheter shaft from a first material having a first hardness. The method further comprises injection molding a first section of a distal tip and placing the first section of the distal tip and a distal end of the catheter shaft in a mold. Finally, the method comprises injection molding a second section of the distal tip within the mold, the second section joining the catheter shaft and the first section, wherein the second section is formed from a second material having a second hardness. In some embodiments, the first section is formed from a third material having a third hardness, the first hardness being greater than the second hardness, and the second hardness being greater than the third hardness.

In some embodiments, the method further comprises placing the first section on a mandrel inside the mold.

In some embodiments, a catheter comprises a catheter shaft and a catheter tip, the catheter shaft comprising a first polymeric material and the catheter tip comprising a second and third polymeric material. The first, second, and third polymeric materials comprise an oligomer common to all of the first, second, and third polymeric materials. In some embodiments, the catheter tip comprises a first longitudinal section and a second longitudinal section, the second longitudinal section formed of a second polymeric material having a second durometer and the first longitudinal section formed of the third polymeric material having a third durometer less than the second durometer. The first longitudinal section is distal to the second longitudinal section and the second longitudinal section is bonded to the catheter shaft and to the first longitudinal section. The first polymeric material has a first durometer greater than the second durometer. At least a portion of the first longitudinal section is tapered and at least a portion of the second longitudinal section is tapered.

BRIEF DESCRIPTION OF THE SEVERAL VIEWS OF THE DRAWING(S)

Figure 2:
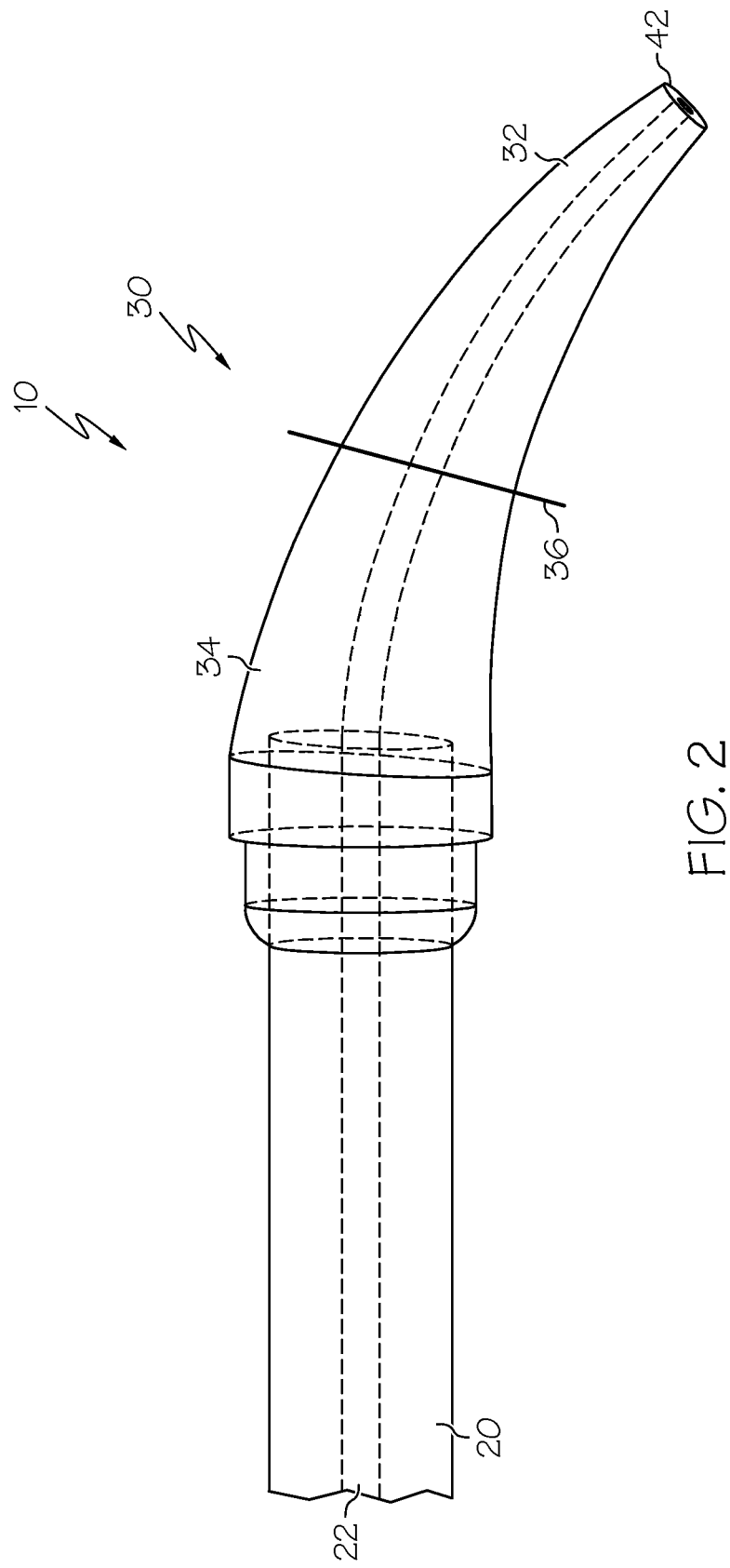
Figure 3:
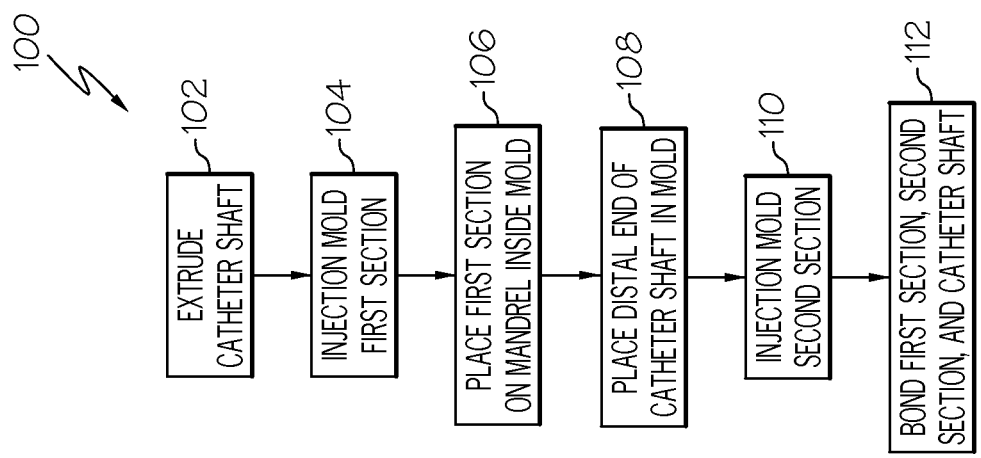

FIG. 1 shows an embodiment of a catheter shaft and tip.
FIG. 2 shows the embodiment of FIG. 1 in a bent configuration.
FIG. 3 shows a method of forming a catheter shaft and tip.

DETAILED DESCRIPTION OF THE INVENTION

While this invention may be embodied in many different forms, there are described herein specific embodiments. This description is an exemplification of the principles of the invention and is not intended to limit it to the particular embodiments illustrated.

For the purposes of this disclosure, like reference numerals in the figures shall refer to like features unless otherwise indicated.

As shown in FIGS. 1 and 2, a catheter 10 comprises a catheter shaft 20 and a distal tip 30. In some embodiments, the catheter shaft 20 may comprise a cylindrical tube having a guide wire lumen 22 disposed therethrough. The distal tip 30 comprises at least a first longitudinal section 32 or first section 32 and a second longitudinal section 34 or second section 34. The first and second sections 32, 34 comprise materials of different hardness from one another. In some embodiments, for example as shown in FIGS. 1 and 2, the first section 32 is longitudinally offset from the second section 34. In embodiments, the first section 32 is distal to the second section 34. Moreover, the first and second sections 32, 34 do not overlap, as illustrated by the dividing line 36. Although in some embodiments the first section 32 is distal to second section 34, where at least one the first and second sections 32, 34 is at least partially melted (described in greater detail below) during formation of the catheter 10, a limited amount of intermingling of the respective materials can occur at the melt interface. In some embodiments, the transition between the first section 32 and the second section 34, along the outer surface of the distal tip 30, is smooth, such that the distal tip 30 does not catch or hang up during insertion of the catheter 10 into a body lumen.

In some embodiments, the first section 32 has a frusto-conical shape, tapering from a larger cross-section at the proximal end 40 of the first section 32 to a smaller cross-section at the distal end 42 of the first section 32. In some embodiments, for example as shown in FIG. 1, the taper of the first section 32 is the same as the taper of the second section 34. Stated differently, the rate of taper is the same for both the first and second sections 32, 34.

In some embodiments, the second section 34 comprises a proximal portion 44, a first cylindrical portion 46, a second cylindrical portion 48, and a frusto-conical portion 50. The frusto-conical portion 50 tapers from a larger cross-section at the proximal end 52 thereof to a smaller cross-section at the distal end 54 of the frusto-conical portion 50. The distal end 54 of the frusto-conical portion 50 abuts the proximal end 40 of the first section 32. And, the second cylindrical portion 48 is disposed between the first cylindrical portion 46 and the frusto-conical portion 50. Finally, the first cylindrical section 46 is disposed between the proximal portion 44 and the second cylindrical portion 48.

In some embodiments, for example as shown in FIGS. 1 and 2, the proximal portion 44, first cylindrical portion 46, and second cylindrical portion 48 extend over a portion of the catheter shaft 20. Further, in some embodiments, a portion of the frusto-conical portion 50 overlaps a portion of the catheter shaft 20.

In some embodiments, the proximal portion 44 is tapered from a smaller cross-section at its proximal end 56 to a larger cross-section at its distal end 58. The distal end 58 of the proximal portion 44 abuts the first cylindrical portion 46, which has the same diameter, or cross-section, along its entire length.

Distal to the first cylindrical portion 46 is the second cylindrical portion 48. The second cylindrical portion 48 has a greater diameter, or cross-section, than the first cylindrical portion 46. The second cylindrical portion 48 has the same diameter, or cross-section, along its entire length. Distal to the second cylindrical portion 48 is the frusto-conical portion 50, and the transition between the second cylindrical portion 48 and the frusto-conical portion 50 is smooth, with the frusto-conical portion 50 tapering along its length.

In some embodiments, the catheter shaft comprises a polymeric material, for example polyether block amide. In particular, in some embodiments, the catheter shaft 20 comprises a polyether block amide sold under the tradename PEBAX® 6333. Other suitable materials such as PEBAX® 7233, polyetherimide, polyetheretherketone, polyamides (e.g., nylon(s)), polyethylene(s), and polypropylene(s).

In some embodiments, the distal tip 30 comprises a polymeric material, for example a polyether block amide. Moreover, in some embodiments, both the first section 32 and the second section 34 of the distal tip 30 comprise a polymeric material, for example polyether block amide. The polyether block amide material of the first section 32 is different from the polyether block amide material of the second section 34. In some embodiments, for example, the polyether block amide polymer of the first section 32 is PEBAX® 2533. Additionally, in some embodiments, the polyether block amide polymer of the second section 34 is PEBAX® 3533. Alternatively, in some embodiments, the polyether block amide polymer of the second section 34 is PEBAX® 4033.

In some embodiments, the second section 34 comprises a polymeric material that has a common oligomer with the polymeric material of the shaft 20, such that the materials bond to one another in an overmolding process, but has a lower durometer than that of the catheter shaft 20. Further, in some embodiments, the first section 32 comprises a polymeric material that has a common oligmer with the polymeric material of the second section 34, but has a lower durometer than that of the second section 34. In this way, in some embodiments each of the first section 32, second section 34, and catheter shaft 20 comprise polymeric materials of similar molecular structure but differing durometer.

In some embodiments, the first and/or second sections 32, 34 are softened or reinforced with additives or pores.

In some embodiments, the catheter shaft 20 and the first and second sections 32, 34 of the distal tip 30 comprise polyether block amide material, though the polyether block amide material of each of the catheter shaft 20 and the first and second sections 32, 34 has different material properties. In some embodiments the hardness of the material of the catheter shaft 20 is greater than that of the first and second sections 32, 34. Moreover, in some embodiments, the hardness of the material of the second section 34 is greater than that of the first section 32. Also, in some embodiments, the tensile strength of the material of the catheter shaft 20 is greater than that of the first and second sections 32, 34. In some embodiments, the material of the first section 32 has a hardness between 20 and 30 shore D, and, in some embodiments, 27 shore D. In some embodiments, the material of the second section 34 has a hardness between 23 and 45 shore D, in some embodiments, between 30 and 42 shore D, in some embodiments, 33 shore D, and in some embodiments, 42 shore D. In some embodiments, the material of the catheter shaft 20 has a hardness between 55 and 70 shore D, and, in some embodiments, 64 shore D.

In some embodiments, the tensile strength of the material of the second section 34 is greater than that of the first section 32. Finally, in some embodiments, the material of the first section 32 is more flexible than the material of the second section 34 and the material of the second section 34 is more flexible than the material of the catheter shaft 20.

In some embodiments, formation of the catheter 10 involves molding the distal tip 30 and extruding the catheter shaft 20. A method of forming a catheter 10 is shown, for example, in FIG. 3 at reference numeral 100. The method 100 comprises extruding 102 the catheter shaft 20, injecting molding 104 the first section 32, placing 106 the first section 32 on a mandrel inside of a mold, placing 108 the distal end of the catheter shaft 20 inside the mold, injection molding 110 the second portion 34, and bonding 112 the first section 32, second section 34, and catheter shaft 20 into a unitary piece.

With additional regard to method steps 106-112, after the first section 32 is molded, it is placed over a mandrel inside a mold. The distal end of the catheter shaft 20 is also inserted into the mold. Subsequently, the material for the second section 34 is injected into the mold. After the material forming the second section 34 has adequately set, it connects the first section 32 to the catheter shaft 20, thereby forming a unitary structure that includes the first section 32, the second section 34, and the catheter shaft 20.

In some embodiments, the method 100 of forming the catheter 10 includes insert molding and/or over molding. In some embodiments, during formation of the catheter 10, the material used to form the first section 32 is melted by the material used to form the second section 34, at the interface or dividing line 36, as the material used to form the second section 34 is introduced into the mold. This interaction of materials forms a cohesive bond on a molecular level at the material interface 36.

During the injection molding process, the material used to form the second section 34 must be compatible with the material used to form the first section 32 and simultaneously compatible with the material used to form the catheter shaft 20 in order to form a cohesive bond. The molding process, temperatures, pressures, flow speeds, and cure times must all be optimized in order for effective interface bonding to occur. This results in good mechanical strength between the varying durometer materials.

Where the catheter shaft 20, first section 32, and second section 34, are each comprised of a polyether block amide material, even of a different durometer, the resulting catheter 10 has good shaft-to-tip bond strength. Additionally, where the first section 32 is made of a softer material than the second section 34 and the catheter shaft 20, the catheter 10 has requisite stiffness to be pushed while also having a distal tip 30 that is soft enough to prevent damage to the patient's organs.

In some embodiments, the dividing line 36 between the first and second sections 32, 34 is half way between the distal end 42 of the first section and the proximal end 56 of the proximal portion 44. In some embodiments, however, the dividing line 36 is more proximal or more distal than as shown in FIG. 1. In particular, in the event that the dividing line 36 is moved distally, the distal tip 30 is stiffer. Conversely, to make the tip less stiff, the dividing line 36 is moved proximally. In this way, the distal tip 30 can take on the desired stiffness by varying the extent to which the respective materials extend along the length of the distal tip 30.

In some embodiments, the catheter 10 is used in the esophageal, biliary, colonic, or duodenal strictures. The catheter 10 can also be used in any suitable body lumen, organ, or orifice.

In some embodiments, the distal tip 30 comprises a straight, cylindrical, hemispherical, oblong, or any other suitable shape.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A catheter comprising:
   a catheter shaft and a catheter tip, the catheter shaft comprising a polyether block amide material and the catheter tip comprising a polyether block amide material, the catheter tip comprising a first longitudinal section and a second longitudinal section joined to the first longitudinal section at a junction therebetween, the first longitudinal section formed of polyether block amide having a first durometer and the second longitudinal section formed of a polyether block amide having a second durometer greater than the first durometer, the first longitudinal section being distal to the second longitudinal section and the second longitudinal section being bonded to the catheter shaft and to the first longitudinal section, the polyether block amide material of the catheter shaft having a third durometer greater than the second durometer, at least a portion of the first longitudinal section being tapered and at least a portion of the second longitudinal section being tapered;

wherein the catheter tip includes a guidewire lumen extending through the tapered portion of the first longitudinal section and the tapered portion of the second longitudinal section, and wherein the guidewire lumen extends to a distalmost extent of the catheter tip;

wherein the first longitudinal section is longitudinally offset from the second longitudinal section such that the polyether block amide having the first durometer and the polyether block amide having the second durometer do not longitudinally overlap.

2. The catheter of claim 1, wherein the material of the first longitudinal section has a durometer between 20 and 30 shore D.

3. The catheter of claim 2, wherein the material of the second longitudinal section has a durometer between 30 and 42 shore D.

4. The catheter of claim 3, wherein the material of the catheter shaft has a durometer between 55 and 70 shore D.

5. The catheter of claim 4, wherein the material of the first longitudinal section has a durometer of 27 shore D and the material of the catheter shaft has a durometer of 64 shore D.

6. The catheter of claim 1, wherein the second longitudinal section comprises a proximal portion, a first cylindrical portion, a second cylindrical portion, and a frusto-conical portion, the first cylindrical portion distal to the proximal portion, the second cylindrical portion distal to the first cylindrical portion, and the frusto-conical portion distal to the second cylindrical portion and proximal to the first longitudinal section.

7. The catheter of claim 6, wherein the proximal portion has a circular cross-section and its diameter increases from the proximal end to the distal end thereof.

8. The catheter of claim 6, wherein the distal end of the catheter shaft extends distally beyond the proximal portion, first cylindrical portion, and second cylindrical portion and into the frusto-conical portion.

9. The catheter of claim 1, wherein the catheter tip has a length and each of the first longitudinal section and second longitudinal section is one-half the length.

10. The catheter of 1, wherein the frusto-conical portion and the first longitudinal section have the same rate of taper.

11. The catheter of claim 1, wherein a distally facing surface of the second longitudinal section abuts a proximally facing surface of the first longitudinal section at the junction.

12. The catheter of claim 1, wherein the first longitudinal section consists of the polyether block amide having the first durometer and the second longitudinal section consists of the polyether block amide having the second durometer.

13. The catheter of claim 1, wherein the polyether block amide having the first durometer fully surrounds the guidewire lumen in the first longitudinal section and the polyether block amide having the second durometer fully surrounds the guidewire lumen in the second longitudinal section.

14. The catheter of claim 13, wherein the polyether block amide having the first durometer extends to an inner surface of the catheter tip defining the guidewire lumen in the first longitudinal section and the polyether block amide having the second durometer extends to the inner surface of the catheter tip defining the guidewire lumen in the second longitudinal section.

15. A catheter comprising:
a catheter shaft and a catheter tip, the catheter tip comprising a first polymeric material and a second polymeric material, and the catheter shaft comprising a third polymeric material, the first, second, and third polymeric materials comprising an oligomer common to all of the first, second, and third polymeric materials;
the catheter tip comprising a first longitudinal section and a second longitudinal section joined to the first longitudinal section at a junction, the first longitudinal section having a proximal end joined to a distal end of the second longitudinal section at the junction such that the first longitudinal section extends distally from the junction and the second longitudinal section extends proximally from the junction, the first longitudinal section consisting of the first polymeric material having a first durometer and the second longitudinal section consisting of the second polymeric material having a second durometer, the first durometer being less than the second durometer, the first longitudinal section being distal to the second longitudinal section and the second longitudinal section being bonded to the catheter shaft and to the first longitudinal section, at least a portion of the first longitudinal section being tapered and at least a portion of the second longitudinal section being tapered; and
wherein the catheter tip includes a guidewire lumen extending through the tapered portion of the first longitudinal section and the tapered portion of the second longitudinal section, and wherein the guidewire lumen extends to a distalmost extent of the catheter tip.

16. The catheter of claim 15, wherein the first longitudinal section and the second longitudinal section do not longitudinally overlap.

17. A catheter comprising:
a catheter shaft comprising a polyether block amide material; and
a catheter tip secured to a distal end of the catheter shaft, the catheter tip including a first longitudinal section formed of a first polyether block amide material having a first durometer and a second longitudinal section formed of a second polyether block amide material having a second durometer greater than the first durometer, the second longitudinal section joined to the first longitudinal section at a junction therebetween;
wherein the first polyether block amide material has a proximal end that terminates at the junction and the second polyether block amide material has a distal end that terminates at the junction, wherein the proximal end of the first polyether block amide material is bonded to the distal end of the second polyether block amide material at the junction;
wherein the first polyether block amide material extends distal from the junction toward a distalmost extent of the catheter tip beyond the second polyether block amide material;
wherein the second polyether block amide material extends proximal from the junction toward a proximal end of the catheter tip beyond the first polyether block amide material;
wherein the polyether block amide material of the catheter shaft has a third durometer greater than the second durometer;
wherein at least a portion of the first longitudinal section being tapered and at least a portion of the second longitudinal section being tapered; and wherein the catheter tip includes a guidewire lumen extending through the tapered portion of the first longitudinal section, and the tapered portion of the second longitudinal section, and wherein the guidewire lumen extends to the distalmost extent of the catheter tip.

18. The catheter of claim 17, wherein the first longitudinal section is longitudinally offset from the second longitudinal section such that the first longitudinal section and the second longitudinal section do not longitudinally overlap.

19. The catheter of claim 17, wherein a distally facing surface of the second longitudinal section abuts a proximally facing surface of the first longitudinal section at the junction, the distally facing surface located at the distal end of the second longitudinal section and the proximally facing surface located at the proximal end of the first longitudinal section.

20. The catheter of claim 17, wherein the first polyether block amide material is located at an inner surface of the first longitudinal section that defines a first portion of the guidewire lumen and the second polyether block amide material is located at an inner surface of the second longitudinal section that defines a second portion of the guidewire lumen proximal of the first portion of the guidewire lumen.

* * * * *